United States Patent [19]
Chio et al.

[11] Patent Number: 5,721,132
[45] Date of Patent: Feb. 24, 1998

[54] SYNTHETIC GENE FOR D4 DOPAMINE RECEPTORS

[75] Inventors: Christopher L. Chio; Rita M. Huff, both of Kalamazoo, Mich.

[73] Assignee: The Upjohn Company, Kalamazoo, Mich.

[21] Appl. No.: 434,877

[22] Filed: May 3, 1995

Related U.S. Application Data

[62] Division of Ser. No. 86,439, Jul. 1, 1993, Pat. No. 5,468,615.

[51] Int. Cl.$^6$ .............................. C12N 5/10; C12N 15/12
[52] U.S. Cl. .................. 435/252.3; 435/69.1; 435/320.1; 536/23.5
[58] Field of Search .......................... 438/69.1, 252.3, 438/320.1; 536/23.5

[56] References Cited

U.S. PATENT DOCUMENTS 4,683,195  7/1987  Mullis et al. ............................ 435/6
5,422,265  6/1995  Civelli et al. ........................ 435/252.3

FOREIGN PATENT DOCUMENTS

WO92/10571  6/1992  WIPO.

OTHER PUBLICATIONS

Chio, C. et al., "D4 dopamine receptor-mediated signaling events determined in transfected Chinese Hampster Ovary cells," J. Biol. Chem., 269(16):11813–11819 (1994).

McHale, M. et al., "Expression & functional characterisation of a synthetic version of the human D$_4$ dopamine receptor in a stable human cell line," FEBS Letters, 345:147–150 (1994).

VanTol, H.H.M., Bunzow, J.R., Guan, H.-C., Sunahara, R.K. Seeman, P. Niznik, H.B., and Civelli, O. (1991) Nature 350:610–614.

Mills, A., Allet, B., Bernard, A., Chabert, C., Brandt, E., Cavegn, C., Chollet, A. and E. Kawashima (1993) FEBS Lett. 320:130–134.

Horton, R.M., Hunt, H.D., Ho, S.N., Pullen, J.K., and Pease, L.R. (1989) Gene 77:61–68.

Sawadago, M. and VanDyke, M.W. (1991) Nucleic Acids Res. 19:674.

Sambrook, J., Fritsch, E.F., and Maniatis, T. (1989) Molecular Cloning–No Copy Enclosed.

Yates, J.L., Warren, N., and Sugden, B. (1985) Nature 313:812–815.

VanTol, H.H.M., Wu, C.M., Guan, H.-C., Ohhara, K., Bunzow, J.R., Civelli, Ol., Kennedy, J. Seeman, Pl. Nizmik, H.B., and Jovanovic, V. (1992) Nature 358:149–152.

*Primary Examiner*—John Ulm
*Attorney, Agent, or Firm*—James D. Darnley, Jr.

[57] ABSTRACT

A modified gene coding for the human D4 dopamine receptor has been synthesized by chemo-enzymatic methods. The nucleotide sequence of the D4 dopamine receptor gene was changed to reduce the G+C content and to eliminate intronic sequences, while maintaining the published amino acid sequence. Using gene splicing by overlap extension and PCR amplification of long oligonucleotides (>200 bases), 3 synthetic fragments of about 400 base pairs each were amplified, from which the full length gene was assembled. Stable expression of this gene has been achieved in CHO-K1 cells, using an inducible expression system, and in HEK293 cells.

5 Claims, 20 Drawing Sheets

FIGURE 1A

```
SynD4   CCACCATGGGTAACAGATCTACTGCAGACGGCAGACGGACTACTTGCTGGA
Match   ||||  |||    |||  || ||  ||||||| ||||  ||  |||||
HumD4   ATGGGGAACCGCAGCACCGGCGGACGCGGACGGGCTGCTGGCTGG
Diff.          G  C CAGC  C    G       G    G    G    G
                                                      100
SynD4   AGAGGTCCAGCTGCAGGAGCTTCTGCTCTGGAGCATCCGCTGACTTGCTGG
Match     ||  |||| ||||| |||| ||  |||||||| |||| || |||||
HumD4   CGCGGGGCCCGGCCCGGGGGCATCTGCGGGGCATCTGGCTGG
Diff.   C C  G  G  G  G  A    G  G    T  G   G   G
SynD4   TCAAGGAGCTGCAGCTTTAGTTGGTGGAGTGTTGTTAATTGGTGCAGTAT
Match    ||  ||  || ||||| |||||||||||||| ||  |||||||| ||
HumD4   GCAGGGCGCGGCCGCTGGTGGGGGCGTGCTGCTCATCGGCGCGGTGC
Diff.   G G C G  G  G  GC G  G  G  C C  C C  C  G  GC
                                                      200
SynD4   TAGCTGGAAACAGTCTAGTTTGTGTTAGTGTAGCAACTGAAAGAGCTCTA
Match    ||  |||||| |||  ||  ||||  || ||| || |  |||||||
HumD4   TCGCGGGAACTCGCTCGTGTGCGTCGTGAGCGTGGCCACCGAGCGCCCTG
Diff.   C  G G  TCG C G C G C G  C G  GC C C C  G
SynD4   CAAACACCTACTAACTCATTCATAGTAAGTTTAGCAGCTGCAGATTATT
Match    ||  | ||  || |||  || |||||| |||||| |||||||
HumD4   CAGACGCCCACCAACTCCTTCATCGTGAGCCTGGCCGCCGACCTCCT
Diff.   G G  G  C   C   C  G  CC G  C  CG  C  CC CC SynD4
Match
HumD4
Diff.
```

FIGURE 1B

```
          300
SynD4  GCTAGCTTTACTTGTACTACCATTATTTGTTTACTCAGAAGTCCAGGGTG
Match  ||| ||   || || || ||   || ||  ||| ||||| |||||||||
HumD4  CCTCGCTCTCCTGGTGCTGCCGCTCTTCGTCTACTCCGAGGTCCAGGGTG
Diff.   C  C  C  C  G G  G  GC C  C  C   G SynD4  GAGCTTGGCTCTCTTAAGTCCAAGATTGTGTGACGCCACTCATGGCAATGGAC
Match  | ||  ||||| ||    ||||    ||||||||| ||||||||| |||||
HumD4  GCGCTGGCTGCTGAGCAGCCCCCGCCTGTGTGACGCCCCTCATGGCCATGGAC
Diff.   C  G  GC G  C  CC CC  C          C         C 400
SynD4  GTCATGTTGTGTACTGCTTCAATTTCAACTTGTGTGCAATCAGTGTAGA
Match  ||||||| |||   ||||| |||| |||| | ||||||||||| |||
HumD4  GTCATGCTGTGCACCGCCTCCATCTTCAACCTGTGCGCCATCAGCGTGA
Diff.          C  C  C  C  CC    C     C  C    C   G SynD4  TCGATTCGTAGCAGTTGCTGTACCATTAAGATACAACAGACAAGGAGGCA
Match  || || ||| |||| |||||  |||| |||||| ||||||| |||| |
HumD4  CAGGTTCGTGGCCGTGGCCGTGGCCAT CAACCGGGCAGGGTGGGA
Diff.   CA  G    G  C  G  G  GC GC C      CG G  T  G 500
SynD4  GTCGACGCCCAGCTGCTTCTCATTGGAGCTACATGGTTACTATCAGCGGCC
Match  |||| ||||||||||||||  || ||||| || ||  ||| ||||| |||
HumD4  GCCGCCCGGGGCCAGCTGCTGCTGCTCATCGGCGCCCACGTGGCTGTCCGGGCG
Diff.   C  C  G        C   C  C  C  C  G   G   C  G
```

FIGURE 1C

```
SynD4   GTAGCTGCACCTGTACTGTGTGGATTGAATGATGTTAGAGGAAGGATCC
Match   || ||  ||||||| ||||| ||| || ||  || || ||||| |||
HumD4   GTGGCGGGCCCGCTACTGTGCGGGCCTCAACGACGTGCGGCCGCCGACCC
Diff.   G  G   G  C          C      CC C C  GC C   CC C  C 600
SynD4   AGCTGTATGTAGATTGGAAGATAGAGATTATGTAGTTTACTCGAGTGTAT
Match   ||  || || |||| ||   || | ||  ||| ||  |||| | |
HumD4   CGCCCGTGCCGCCTGGAGGACCGGACTACGTGGTCTACTCGTCCGTGT
Diff.   C  C  G CC CC    G  CC CC G    CCCC G C      TCC  G SynD4   GTAGTTTCTTTCTACCATGTCCATTAATGTTGCTACTTTACTGGGCAACA
Match    |||||  || ||| |   || ||    ||| |||| | |||||||||
HumD4   GCTCCTTCTTCCTACCCCTGCCTCATGCTGCTGCTCTACTGGGCCACG
Diff.   CTCC       C    C  C  GC C   C    C  G        C  G 700
SynD4   TTCAGAGGACTGCAGAGATGGGAAGTTGCACGTCGTGCAAAGTTACATGG
Match   ||| || || ||||   |||  || ||||| |||||||  ||| ||||
HumD4   TTCCGGCCTGCAGCGGTGGAGGTGGCACGTGGCACCGCCAAGCTGCACGG
Diff.   C C     C   C   G    G    G    C  C C    C G  C
```

FIGURE 1D

```
SynD4   AAGAGCACCAAGAAGAGACCTGGACCTGGACCACCTAGTCCAACACCTC
Match   ||||| |||  ||||  | |||||||||| ||||| |||||| ||||
HumD4   CCGGCGCCCCGCCGGACCCCGCCGACCCCGGACTGGCCCTTCCCCACGCCAC
Diff.        CC  C    G  CC  CC     C    C    CG   TCC  C G    A SynD4   CAGCTCCAAGATTACCTCAAGATCCTTGTGGGCCCGACTGTGCTCCTCCA
Match   | ||||||||   ||| |||||  |||||  || |||||||||| |||
HumD4   CCGCGCCCCGCCCTGCCCCAGGACCCCTGTGCGCCCTGCGGCCCCC
Diff.    C  G     CC CC  C  C    C    GC  C    G  C        G   CC SynD4   GCACCTGGTTTACCTCCAGATCCTTGTGGTTCTAACTGTGCTCCTCCAGA
Match   || || | |  || ||||| |||| | ||||  ||  |||||| |||||
HumD4   GCGCCCGGCCTTCCCCGGACCCCTGCGCTCCAACTGTGCTCCCCCCGA
Diff.    G C  C      CC     C  C  CGCCC  C  CC    C           C SynD4   TGCGGTCCGAGCTGCAGCTCTACCACCTCAGACTCCACCTCAGACGCGTA
Match   |  ||||||  ||||| || ||||||| | ||||  |||| ||  |  |
HumD4   CGCCGTCAGAGCCGCGCCGTCCCACCCCAGACCCCAGACCCCGCA
Diff.    C  C    A     C    C G  C  C         CC       G   CCC   C SynD4   GGAGAAGGAGAGCTAAAGATCACAGGAAGGGAGAAAGCTATGAGGGTC
Match   |||| ||  |||| || |||||  | |||| ||||  ||||| |||||
HumD4   GGAGGCGGGCGTGCCAAGATCACCGGCCGAGGCCAAGGCCATGAGGGTC
Diff.              GC    C T   C         CC      CCG    C      CC C
```

FIGURE 1E

```
SynD4    CTACCTGTGTCGTTGGTGTGCATTCTTGTTATGCTGGACACCATTCTTTGT
Match    ||  |||||  |||  ||||   ||| ||||||||||||   || |||||
HumD4    CTGCCGGTGGTGTGGTCGGGGCCTTCCTGCTGTGCTGGACGCCCTTCTTCGT
Diff.    G   G   GCG    C  C    CCG              G  C   C                                    1000

SynD4    TGTGCACATCACACAAGCACTGTGTCCTGCTCCTTGCTCAGTGCCACCTAGAC
Match    ||||||||||  ||  ||  || |||||||| || ||||||||||||
GGTGCACATCACGCAGGCGCTGTGTCCTGCCCGTGCTCAGTGCCCCCGCGGC
Diff.    G       G  G   G  G                C   C     CC GC G SynD4    TTGTCAGTGCGGTCACCCTGGTTGGGTTACGTAAACTCAGCACTCAATCCT
Match    | |||| |||||||||| ||||  || ||| |||||||| ||||||
TGGTCAGCCGCGGTCACCCTGGCCCTGGGCTACGTGGGCTCAACAGCCCCTCAACCCC
Diff.    G    C C          C  C   C       AGC    C   C SynD4    GTCATCTACACTGTATTCAATGCTGAATTCAGAAATGTCTTCAGAAAAGGC
Match    ||||||||||| |||| |||| |||| || ||||||||||||||  ||||
GTCATCTACACTGTCTTCAACGCCCGAGTTCCGCAACGTCTTCCGCAAGGC
Diff.             C   C    G   C    C  C  C   C   C    C SynD4    TCTAAGAGCTTGCCTGCTGA    1169
Match    ||   | ||||| ||||||||
CCTGCCGTGCCCTGCTGCTGA
Diff.    C  GC T  C
```

FIGURE 2A

```
            B
        N   g
        c   l
        o   I
        I   I
      CCACCATGGGTAACAGATCTACTGCAGACGCAGACGGACTACTTGCTGGA
   1  ---------+---------+---------+---------+---------+ 50
      GGTGGTACCCATTGTCTAGATGACGTCTGCGTCTGCCTGATGAACGACCT

M  G  N  R  S  T  A  D  A  D  G  L  L  A  G  -

F
                    o
                    k
                    I
      AGAGGTCCAGCTGCAGGAGCTTCTGCTGGAGCATCCGCTGGACTTGCTGG
  51  ---------+---------+---------+---------+---------+ 100
      TCTCCAGGTCGACGTCCTCGAAGACGACCTCGTAGGCGACCTGAACGACC

R  G  P  A  A  G  A  S  A  G  A  S  A  G  L  A  G  -

TCAAGGAGCTGCAGCTTTAGTTGGTGGAGTGTTGTTAATTGGTGCAGTAT
 101  ---------+---------+---------+---------+---------+ 150
      AGTTCCTCGACGTCGAAATCAACCACCTCACAACAATTAACCACGTCATA

Q  G  A  A  A  L  V  G  G  V  L  L  I  G  A  V  L  -

S
                                                 a
                                                 c
                                                 I
      TAGCTGGAAACAGTCTAGTTTGTGTTAGTGTAGCAACTGAAAGAGCTCTA
 151  ---------+---------+---------+---------+---------+ 200
      ATCGACCTTTGTCAGATCAAACACAATCACATCGTTGACTTTCTCGAGAT

```
         CAAACACCTACTAACTCATTCATAGTAAGTTTAGCAGCTGCAGATTTATT
201      ---------+---------+---------+---------+---------+  250
         GTTTGTGGATGATTGAGTAAGTATCATTCAAATCGTCGACGTCTAAATAA

Q  T  P  T  N  S  F  I  V  S  L  A  A  A  D  L  L   -
                                              N
                                              h
                                              e
                                              I

GCTAGCTTTACTTGTACTACCATTATTTGTTTACTCAGAAGTCCAGGGTG
251      ---------+---------+---------+---------+---------+  300
         CGATCGAAATGAACATGATGGTAATAAACAAATGAGTCTTCAGGTCCCAC

L  A  L  L  V  L  P  L  F  V  Y  S  E  V  Q  G  G  -
                       A
                       f
                       l
                       I
                       I

GAGCTTGGCTCTTAAGTCCAAGATTGTGTGACGCACTCATGGCAATGGAC
301      ---------+---------+---------+---------+---------+  350
         CTCGAACCGAGAATTCAGGTTCTAACACACTGCGTGAGTACCGTTACCTG

A  W  L  L  S  P  R  L  C  D  A  L  M  A  M  D    -
            A
            a
            t
            I
            I

GTCATGTTGTGTACTGCTTCAATTTTCAACTTGTGTGCAATCAGTGTAGA
351      ---------+---------+---------+---------+---------+  400
         CAGTACAACACATGACGAAGTTAAAAGTTGAACACACGTTAGTCACATCT

V  M  L  C  T  A  S  I  F  N  L  C  A  I  S  V  D  -
                                              C
                                              l
                                              a
                                              I

TCGATTCGTAGCAGTTGCTGTACCATTAAGATACAACAGACAAGGAGGCA
401      ---------+---------+---------+---------+---------+  450
         AGCTAAGCATCGTCAACGACATGGTAATTCTATGTTGTCTGTTCCTCCGT

```
                                                         X
                                                         m
              S                                          a
              a                                          I
              l                                          I
              I                                          I
              GTCGACGCCAGCTGCTTCTCATTGGAGCTACATGGTTACTATCAGCGGCC
     451      ---------+---------+---------+---------+---------+  500
              CAGCTGCGGTCGACGAAGAGTAACCTCGATGTACCAATGATAGTCGCCGG

R   R   Q   L   L   L   I   G   A   T   W   L   L   S   A   A   -

B
                                                          a
                                                          m
                                                          H
                                                          I
              GTAGCTGCACCTGTACTGTGTGGATTGAATGATGTTAGAGGAAGGGATCC
     501      ---------+---------+---------+---------+---------+  550
              CATCGACGTGGACATGACACACCTAACTTACTACAATCTCCTTCCCTAGG

V   A   A   P   V   L   C   G   L   N   D   V   R   G   R   D   P   -

A
                                             v
                                             a
                                             I
              AGCTGTATGTAGATTGGAAGATAGAGATTATGTAGTTTACTCGAGTGTAT
     551      ---------+---------+---------+---------+---------+  600
              TCGACATACATCTAACCTTCTATCTCTAATACATCAAATGAGCTCACATA

A   V   C   R   L   E   D   R   D   Y   V   V   Y   S   S   V   C   -

B
                                                      s
                                                      r
                                                      I
              GTAGTTTCTTTCTACCATGTCCATTAATGTTGCTACTTTACTGGGCAACA
     601      ---------+---------+---------+---------+---------+  650
              CATCAAAGAAAGATGGTACAGGTAATTACAACGATGAAATGACCCGTTGT

```
                                    D
                                    r
                                    a
                                    I
                                    I
                                    I
       TTCAGAGGACTGCAGAGATGGGAAGTTGCACGTCGTGCAAAGTTACATGG
  651  ---------+---------+---------+---------+---------+ 700
       AAGTCTCCTGACGTCTCTACCCTTCAACGTGCAGCACGTTTCAATGTACC

F   R   G   L   Q   R   W   E   V   A   R   R   A   K   L   H   G   -

AAGAGCACCAAGAAGACCTAGTGGACCTGGACCACCTAGTCCAACACCTC
  701  ---------+---------+---------+---------+---------+ 750
       TTCTCGTGGTTCTTCTGGATCACCTGGACCTGGTGGATCAGGTTGTGGAG

R   A   P   R   R   P   S   G   P   G   P   P   S   P   T   P   P   -

A
                                            p
                                            a
                                            I
       CAGCTCCAAGATTACCTCAAGATCCTTGTGGGCCCGACTGTGCTCCTCCA
  751  ---------+---------+---------+---------+---------+ 800
       GTCGAGGTTCTAATGGAGTTCTAGGAACACCCGGGCTGACACGAGGAGGT

A   P   R   L   P   Q   D   P   C   G   P   D   C   A   P   P   -

P
                                        f
                                        l
                                        M
                                        I
       GCACCTGGTTTACCTCCAGATCCTTGTGGTTCTAACTGTGCTCCTCCAGA
  801  ---------+---------+---------+---------+---------+ 850
       CGTGGACCAAATGGAGGTCTAGGAACACCAAGATTGACACGAGGAGGTCT

```
                                                       A
                                                       f
           R                                           l
           s                                           I
           r                                           I
           I                                           I
           I                                           I
        TGCGGTCCGAGCTGCAGCTCTACCACCTCAGACTCCACCTCAGACGCGTA
    851 ---------+---------+---------+---------+---------+ 900
        ACGCCAGGCTCGACGTCGAGATGGTGGAGTCTGAGGTGGAGTCTGCGCAT

A  V  R  A  A  A  L  P  P  Q  T  P  P  Q  T  R  R  -

P
                                                       p
                                                       u
                                                       M
                                                       I
        GGAGAAGGAGAGCTAAGATCACAGGAAGGGAGAGGAAAGCTATGAGGGTC
    901 ---------+---------+---------+---------+---------+ 950
        CCTCTTCCTCTCGATTCTAGTGTCCTTCCCTCTCCTTTCGATACTCCCAG

R  R  R  A  K  I  T  G  R  E  R  K  A  M  R  V  -

CTACCTGTGGTCGTTGGTGCATTCTTGTTATGCTGGACACCATTCTTTGT
    951 ---------+---------+---------+---------+---------+ 1000
        GATGGACACCAGCAACCACGTAAGAACAATACGACCTGTGGTAAGAAACA

L  P  V  V  V  G  A  F  L  L  C  W  T  P  F  F  V  -

A
                p
                a
                L
                I
        TGTGCACATCACACAAGCACTGTGTCCTGCTTGCTCAGTGCCACCTAGAC
   1001 ---------+---------+---------+---------+---------+ 1050
        ACACGTGTAGTGTGTTCGTGACACAGGACGAACGAGTCACGGTGGATCTG

```
                              B
                              s
                              t
                              E
                              I
                              I
         TTGTCAGTGCGGTCACCTGGTTGGGTTACGTAAACTCAGCACTCAATCCT
1051     ---------+---------+---------+---------+---------+ 1100
         AACAGTCACGCCAGTGGACCAACCCAATGCATTTGAGTCGTGAGTTAGGA

V  S  A  V  T  W  L  G  Y  V  N  S  A  L  N  P   -

E
                                       c
                                       o
                                       R
                                       I
         GTCATCTACACTGTATTCAATGCTGAATTCAGAAATGTCTTCAGAAAGGC
1101     ---------+---------+---------+---------+---------+ 1150
         CAGTAGATGTGACATAAGTTACGACTTAAGTCTTTACAGAAGTCTTTCCG

V  I  Y  T  V  F  N  A  E  F  R  N  V  F  R  K  A  -

TCTAAGAGCTTGCTGCTGA
1151     ---------+--------- 1169
         AGATTCTCGAACGACGACT

L  R  A  C  C  *   -
```

Enzymes that do cut:

| AatII | AflII | AflIII | ApaI | ApaLI | AvaI | BamHI |
|-------|-------|--------|------|-------|------|-------|
| BglII | BsrI  | BstEII | ClaI | DraIII | EcoRI | FokI |
| NcoI  | NheI  | PflMI  | PpuMI | RsrII | SacI | SalI |
| XmaIII |

Enzymes that do not cut:

NONE

FIGURE 3A

```
LC49    5'-CACTATAAGCTTCCACCATGGGTAACAGATCTA->
LC61           5'- CCACCATGGGTAACAGATCTACTGCAGACGGCCAGACGGACTACTTGCTGGA
        1      ----------+---------+---------+---------+---------+    50

AGAGGTCCAGCTGCAGGAGCTTCTGCTGGAGCATCCGCTGGACTTGCTGG
        51     ----------+---------+---------+---------+---------+    100

TCAAGGAGCTGCAGCTTTAGTTGGTGTGGAGTGTTGTTAATTGGTGCAGTAT
        101    ----------+---------+---------+---------+---------+    150

TAGCTGGAAACAGTCTAGTTTGTGTTAGTGTAGCAACTGAAAGAGCTCTA
                                                          <-CGAGAT
        151    ----------+---------+---------+---------+---------+    200

CAAACACCTACTAAC->
               GTTTGTGGATGATTGAGTAAGTATCATTCAAATCGTCGACGTCTAAATAA
        201    ----------+---------+---------+---------+---------+    250
```

FIGURE 3B

```
                                                                    300
251 -------+---------+---------+---------+---------+---------+
        CGATCGAAATGAACATGATGGTAATAAACAAATGAGTCTTCAGGTCCCAC 350
301 -------+---------+---------+---------+---------+---------+
        CTCGAACCGAGAATTCAGGTTCTAACACACTGCCGTGAGTACCGTTACCTG 400
351 -------+---------+---------+---------+---------+---------+
        CAGTACAACACATGACGAAGTTAAAAGTTGAACACACGTTAGTCACATCT
                                                      <-AGTCACATCT

401 -------+--  411       CLC62
        AGCTAAGCATC  -5'                              CLC71
        AGCTAAGCATCTTCGAATATCAC  -5'
```

FIGURE 3C

```
LC65 5'- CACTATAAGCTTATCGATTCGTAGCAGTTGCTG->
LC63      5'- ATCGATTCGTAGCAGTTGCTGTACCATTAAGATACAACAGACAAGGAGC    449
          +----+----+----+----+----+----+----+----+----+----+
          400

AGTCGACGCCAGCTGCTTCTCATTGGAGCTACATGGTTACTATCAGCGGC    499
          +----+----+----+----+----+----+----+----+----+----+
          450

CGTAGCTGCACCTGTACTGTGTGGATTGAATGATGTTAGAGGAAGGGATC    549
          +----+----+----+----+----+----+----+----+----+----+
          500

CAGCTGTATGTAGATTGGAAGATAGAGAGATTATGTAGTTTACTCGAGTGTA  599
          +----+----+----+----+----+----+----+----+----+----+
          550                                         <-CAT

TGTAGTTTCTTTCTACCATG->
          +----+----+----+----+----+----+----+----+----+----+  649
          ACATCAAAGAAAGATGGTACAGGTAATTACAACGATGAAATGACCCGTTG
          600
```

FIGURE 3D

```
      +---------+---------+---------+---------+---------+ 699
650   TAAGTCTCCTGACGTCTCTACCCTTCAACGTGCAGCACGTTTCAATGTAC

+---------+---------+---------+---------+---------+ 749
700   CTTCTCGTGGTTCTTCTGGATCACCTGGTGGATCAGGTTGTGGA

+---------+---------+---------+---------+---------+ 799
750   GGTCGAGGTTCTAATGGAGTTCTAGGAACACCCGGGCTGACACGAGGAGG
                                             <--CACGGAGGAGG

+--------- 808                                CLC64
800   TCGTGGACC  -5'                                CLC76
      TCGTGGACCTTCGAATATCAC  -5'
```

FIGURE 3E

```
LC77    5'- CACTATAAGCTTCCAGCACCTGGTTTACCTCC->
LC67    5'- CCAGCACCTGGTTTACCTCCCAGATCCTTGTGGTTCTAACTGTGCTCCTCC      847
            798 ---+---------+---------+---------+---------+---------+
                                                                   848

AGATGCGGTCCGAGCTGCAGCTCTACCACCACCTCAGACTCCACCTCAGACGC      897
            ---+---------+---------+---------+---------+---------+
                                                                   898

GTAGGAGAAGGAGAGCTAAGATCACAGGAAGGGAGAGGAAAGCTATGAGG        947
            ---+---------+---------+---------+---------+---------+
                                                                   948

GTCCTACCTGTGTCGTTGGTGCATTCTTGTTATGCTGGACAC->              997
            ---+---------+---------+---------+---------+---------+
                <--GTAAGAACAATACGACCTGTGGTAAGAA
                                                                   998

--+---------+---------+---------+---------+---------+   1047
            ACAACACGTGTAGTGTGTTCGTGACACAGGACGAACGAGTCACGGTGGAT
```

FIGURE 3F

```
1048 ---+----+----+----+----+----+ 1097
     CTGAACAGTCACGCCAGTGGACCAACCCAATGCATTTGAGTCGTGAGTTA

1098 ---+----+----+----+----+----+ 1147
     GGACAGTAGATGTGACATAAGTTACGACTTAAGTCTTTACAGAAGTCTTT
                                                <-TT

1148 ---+----+----+---- 1169
     CCGAGATTCTCGAACGACGACT     -5'    CLC68
     CCGAGATTCTCGAACGACGACTTCGAATATCAC -5'    CLC70
```

Kd = 100 pM
Bmax = 736 fmol/mg protein

SYNTHETIC GENE FOR D4 DOPAMINE RECEPTORS

CROSS-REFERENCE TO RELATED APPLICATIONS

This application is a divisional of U.S. Ser. No. 08/086,439, filed 1 Jul. 1993, now U.S. Pat. No. 5,468,615.

BACKGROUND OF THE INVENTION

1. Field of the Invention

The invention relates to dopamine receptors and the genes corresponding to such receptors. In particular, it relates to a synthetic dopamine receptor having drug dissociation properties similar to those properties characteristic of the human dopamine receptor D4.

2. Background

Dopamine is a neurotransmitter that participates, in a variety of different functions mediated by the nervous system, including vision, movement, and behavior. See generally Cooper, J. et al. The Biochemical Basis of Neuropharmacology, 161–195 (Oxford University Press, NY 3d Ed. 1978). The diverse physiological actions of dopamine are in turn mediated by its interaction with two of the basic types of G protein-coupled receptors: D1 and D2, which respectively stimulate and inhibit the enzyme adenylyl cyclase. Kebabian, J. and Calne, D., Nature 277: 93–96 (1979). Alterations in the number or activity of these receptors may be a contributory factor in disease states such as Parkinson's disease (a movement disorder) and schizophrenia (a behavioral disorder).

A great deal of information has accumulated on the biochemistry of the D1 and D2 dopamine receptors, and methods have been developed to solubilize and purify these receptor proteins. See Senogles, S. et al., Biochemistry 25: 749–753 (1986); Gingrich, J. et al., Biochemistry 27: 3907–3912 (1988). The D1 dopamine receptor in several tissues appears to be a glycosylated membrane protein of about 72 kDa. Amlaiky, N. et al., Mol. Pharmacol. 31: 129–134 (1987); Niznik, H. et al., Biochemistry 27: 7594–7599 (1988). The D2 receptor has been suggested to have a higher molecular weight of about 90–150 kDa. Amlaiky, N. and Caron, M., J. Biol. Chem. 260: 1983–1986 (1985); Amlaiky, N. and Caron, M., J. Neurochem. 47: 196–204 (1986); Jarvie, J. et al., Mol. Pharmacol. 34: 91–97 (1988). Much less is known about a recently discovered additional dopamine receptor, termed D3. Sokoloff, P. et al. Nature 347: 146–151 (1990). Dopamine receptors are primary targets in the clinical treatment of psychomotor disorders such as Parkinson's disease and affective disorders such as schizophrenia. Seeman, P. et al, Neuropsychopharm. 1: 5–15 (1987); Seeman, P. Synapse 1: 152–333 (1987). The three different dopamine receptors (D1, D2, D3) have been cloned as a result of nucleotide sequence homology which exists between these receptor genes. Bunzow, J. R. et al. Nature 336: 783–787 (1988); Grandy, D. K. et al. Proc. Natl. Acad. Sci. U.S.A. 86: 9762–9766 (1989); Dal Toso, R. et al. EMBO J. 8: 4025–4034 (1989); Zhou, Q-Y. et al. Nature 346: 76–80 (1990); Sunahara, R. K. et al. Nature 346: 80–83 (1990); Sokoloff, P. et al. Nature 347, 146–151 (1990).

The antipsychotic clozapine is useful for socially withdrawn and treatment-resistant schizophrenics [Kane, J. et al. Nature 347: 146–151 (1990)], but unlike other antipsychotic drugs, clozapine does not cause tardive dyskinesia [Casey, D. E. Psychopharmacology 99: 547–553 (1989)]. Clozapine, however, has dissociation constants at D2 and D3 which are 3 to 30-fold higher than the therapeutic free concentration of clozapine in plasma water [Ackenheil, M. et al. Arzneim-Forsch 26: 1156–1158 (1976); Sandoz Canada, Inc., Clozaril: Summary of preclinical and clinical data (1990)]. This suggests the existence of dopamine receptors more sensitive to the antipsychotic clozapine.

Van Tol et al., (1991) Nature, 350:610–614 report that they have cloned and sequenced a D2-like human dopamine receptor which they termed D4. They report that the dopamine D4 receptor gene has high homology to the human dopamine D2 and D3 receptor genes. They further report that the pharmacological profile of this receptor resembles that of the D2 and D3 receptors but that it has an affinity for clozapine which is tenfold higher. Van Tol et al. suggest that this characteristic may make the D4 receptor useful in discovering new types of drugs for schizophrenia that, like clozapine, do not induce tardive dyskinesia and other motor side effects.

Unfortunately, the anticipated low abundance of D4 receptors in the brain based on mRNA studies has hindered studies of the native D4 receptors. In addition, the genomic clone isolated and used by Van Tol et al. for expression contains introns. In a personal communication to the present inventors, H. H. M. Van Tol acknowledged that their expression construct could not be stably expressed. Therefore, a new approach is needed to facilitate the development of cell lines capable of the stable expression of a D4 dopamine receptor gene to further pharmacological and functional analysis of the D4 receptor.

INFORMATION DISCLOSURE

Van Tol, H. H. M., Bunzow, J. R., Guan, H.-C., Sunahara, R. K., Seeman, P., Niznik, H. B., and Civelli, O. (1991) Nature 350: 610–614.

Mills, A., Allet, B., Bernard, A., Chabert, C., Brandt, E., Cavegn, C., Chollet, A. and E. Kawashima (1993) FEBS Lett. 320: 130–134.

Horton, R. M., Hunt, H. D., Ho, S. N., Pullen, J. K., and Pease, L. R. (1989) Gene 77: 6168.

Sawadago, M., and VanDyke, M. W. (1991) Nucleic Acids Res. 19: 674.

Sambrook, J., Fritsch, E. F., and Maniatis, T. (1989) Molecular Cloning.

Yates, J. L., Warren, N., and Sugden, B. (1985) Nature 313: 812–815.

Van Tol, H. H. M., Wu, C. M., Guan, H.-C., Ohhara, K., Bunzow, J. R., Civelli, O., Kennedy, J., Seeman, P., Niznik, H. B., and Jovanovic, V. (1992) Nature 358: 149–152.

SUMMARY OF THE INVENTION

The present invention is directed toward the synthesis of a dopamine receptor corresponding to the nucleotide sequence [SEQ ID NO: 1] shown in the top line of FIG. 2A, B, C, D, E, F. This nucleotide sequence encodes a synthetic gene for D4 dopamine receptor which has an identical amino acid sequence [SEQ ID NO: 3] to the human D4 dopamine receptor. Therefore, the synthesized D4 dopamine receptor has drug dissociation properties similar to those properties characteristic of the human D4 dopamine receptor. For example, the synthetic gene expresses a D4 dopamine receptor which has an affinity for the drug clozapine similar to that displayed by human D4 dopamine receptor.

Synthesizing the human D4 dopamine receptor gene was surprisingly difficult. Attempts to use the polymerase chain reaction to obtain a full length clone for the D4 receptor were unsuccessful, possibly due to the naturally high G+C content of the human D4 dopamine receptor gene [SEQ ID NO: 2]. This problem was surprisingly and unexpectedly overcome by using a chemo-enzymatic approach to construct the synthetic D4 dopamine receptor. While maintaining the published amino acid sequence [SEQ ID NO: 3] for human D4 dopamine receptor, the human D4 dopamine receptor nucleic acid sequence [SEQ ID NO: 2] was modified to reduce its G+C content to 50% from a natural level of 73%. This reduction allows the use of the polymerase chain reaction (PCR) in the synthesis of the synthetic D4 dopamine receptor. Using gene splicing by overlap extension and PCR amplification of long oligonucleotides (>200 mers), 3 synthetic fragments of about 400 base pairs (bp) each were amplified, from which the total gene was assembled. Stable expression of the synthetic gene was achieved in eukaryotic cells such as CHO-K1 cells, by use of an inducible system, and in HEK293 cells.

Transforming a eukaryotic cell culture with an expression vector containing the synthetic D4 dopamine receptor nucleic acid sequence provides for the expression of sufficient amounts of synthetic D4 dopamine receptor protein to allow for the convenient detection of dopamine binding inhibitors and also for the screening of compounds for anti-psychotic activity.

BRIEF DESCRIPTION OF THE DRAWINGS

FIGS. 1A to 1E. Comparison of the modified D4 sequence to the original sequence.

The modified sequence (SynD4) [SEQ ID NO: 1] is aligned with the original human sequence (HumD4) [SEQ ID NO: 2]. The vertical lines indicate matching nucleotides, the bottom line shows the nucleotides that were changed to reduce the G+C content of the gene. Numbers at the ends of the lines correspond to nucleotide position.

FIGS. 2A, B, C, D, E, F. Nucleotide [SEQ ID NO: 1] and amino acid [SEQ ID NO: 3] sequences of the modified D4 gene.

The unique restriction sites are shown above the nucleotide sequence [SEQ ID NO: 1]. Numbers at the ends of the lines indicate nucleotide position.

FIGS. 3A, B, C, D, E, F. Sequences of the templates and primers for the three sections of the modified D4 gene.

The sequence above the number line is the sense strand, and the antisense sequence is below the number line. Numbers at the ends of the lines correspond to the numbering in FIGS. 2A, B, C, D, E, F. Arrows at the 3' ends of the sequences indicate direction of nucleotide addition by Taq polymerase. All of the primers [SEQ ID NOS 4–] have a HindIII site at their 5' ends for subcloning purposes.

Figure 4:
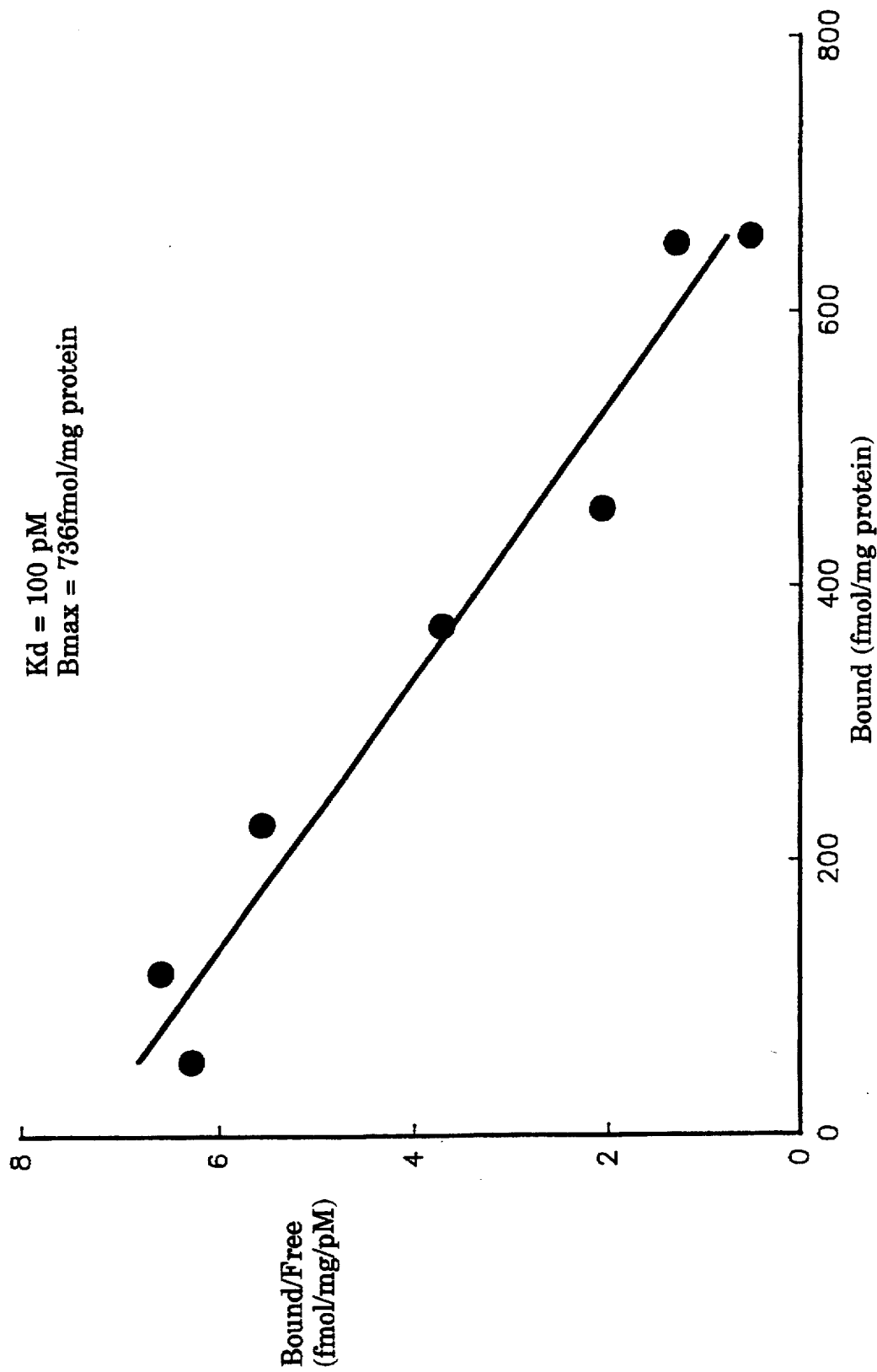

FIG. 4. Scatchard analysis of ($^3$H)-spiperone binding in HEK 293 D4–24 cells.

Shown is a Scatchard transformation of the saturation analysis of the binding of $^3$H-spiperone binding. Each point is the mean of duplicates with non-specific binding subtracted.

Figure 5:
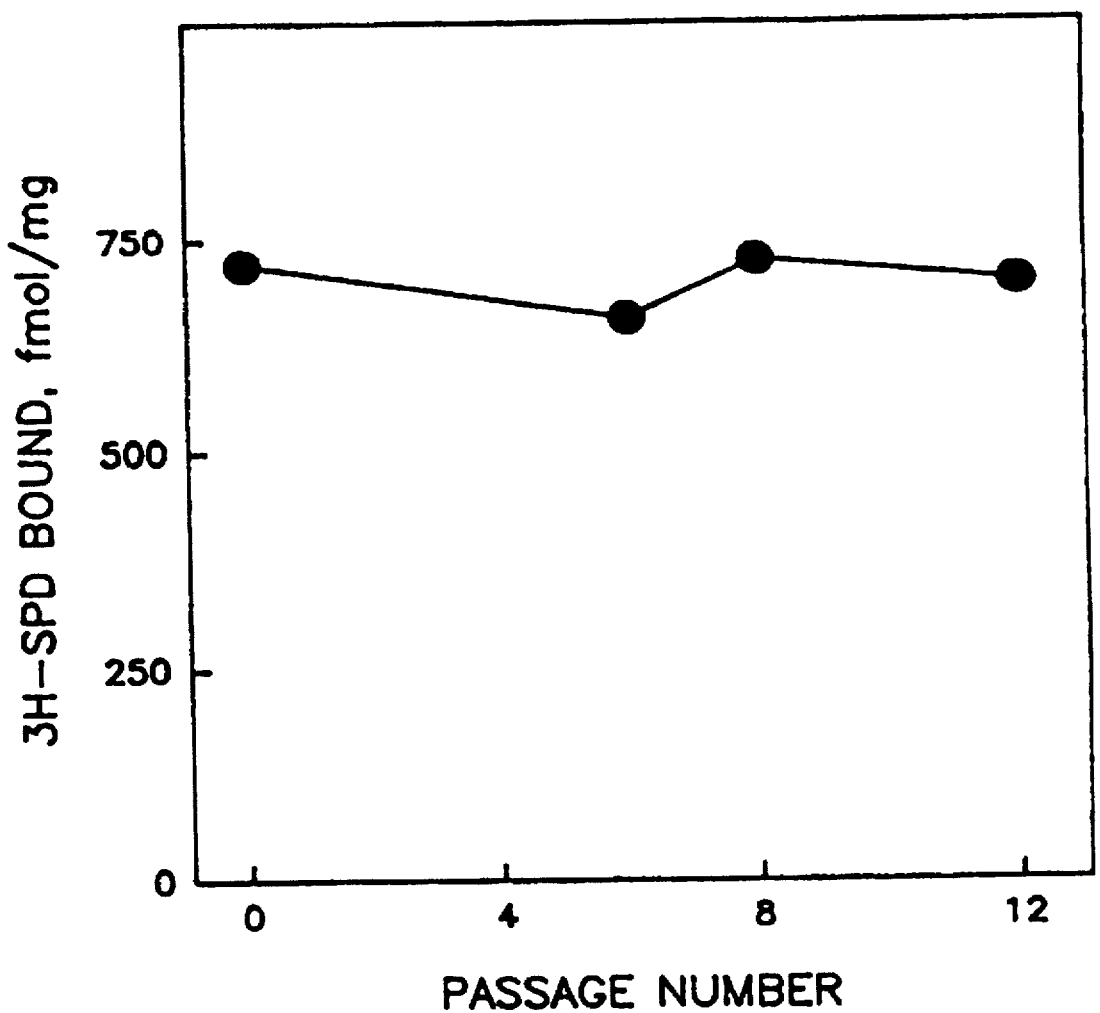

FIG. 5. Stable expression of D4 receptors in HEK 293 D4–24 cells.

$^3$H-spiperone binding at 540 pM was determined in membranes prepared from HEK 293 D4–24 cells harvested at the indicated passage.

Figure 6:
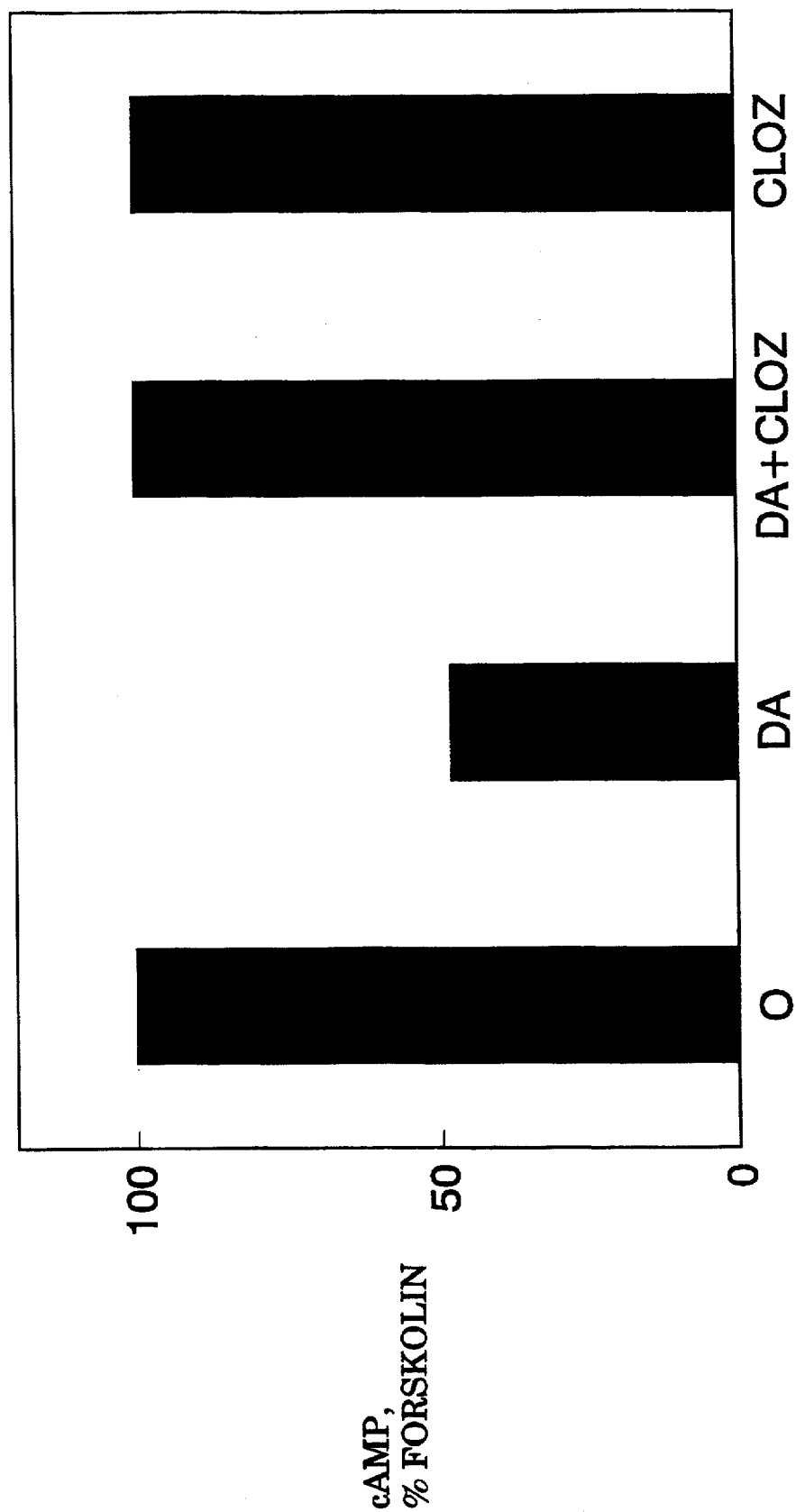

FIG. 6. Inhibition of cAMP accumulation by dopamine in CHO cells expressing D4 receptors. Antagonism by clozapine.

DETAILED DESCRIPTION OF THE PREFERRED EMBODIMENT

The term "synthetic or modified D4 dopamine receptor" as used herein refers to proteins homologous to the protein coded for by the nucleotide sequence depicted in the top line of FIGS. 1A to 1E. The synthetic D4 dopamine receptor has the same amino acid composition as the human D4 receptor. [SEQ ID NO: 3]

Nucleotide bases are abbreviated herein as follows:

| A-Adenine | G-Guanine |
|---|---|
| C-Cytosine | T-Thymine |

Amino acid residues are abbreviated herein to either three letters or a single letter as follows:

| Ala; A-Alanine | Leu; L-Leucine |
|---|---|
| Arg; R-Arginine | Lys; L-Lysine |
| Asn; N-Asparagine | Met; M-Methionine |
| Asp; D-Aspartic acid | Phe; F-Phenylalanine |
| Cys; C-Cysteine | Pro; P-Proline |
| Gln; Q-Glutamine | Ser; S-Serine |
| Glu; E-Glutamic Acid | Thr; T-Threonine |
| Gly; G-Glycine | Trp; W-Tryptophan |
| His; H-Histidine | Tyr; Y-Tyrosine |
| Ile; I-Isoleucine | Val; V-Valine |

The production of proteins such as the D4 dopamine receptor from cloned genes by genetic engineering is well known. The synthetic D4 dopamine receptor may be synthesized in host cells transformed with vectors containing DNA encoding the synthetic D4 dopamine receptor. A vector is a replicable DNA construct. Vectors are used herein either to amplify DNA encoding the synthetic D4 dopamine receptor and/or to express DNA which encodes the synthetic D4 dopamine receptor [SEQ ID NO: 1]. An expression vector is a replicable DNA construct in which a DNA sequence encoding the synthetic D4 dopamine receptor [SEQ ID NO: 1] is operably linked to suitable control sequences capable of effecting the expression of the synthetic D4 dopamine receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the synthetic D4 dopamine receptor vectors constructed using recombinant techniques. Transformed host cells ordinarily express the synthetic D4 receptor, but host cells transformed for purposes of cloning or amplifying the synthetic D4 receptor DNA need not express the synthetic D4 receptor. When expressed, the synthetic D4 receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in the same translational reading frame.

Cultures of cells derived from multicellular organisms are a desirable host for recombinant synthetic D4 dopamine receptor synthesis. In principle, any higher enkaryotic cell culture is workable, whether from vertebrate or invertebrate culture. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are Chinese hamster ovary (CHO) cell lines and HEK293 cells. Expression vectors for such cells ordinarily include (if necessary) an origin of replication, a promoter located upstream from the gene to be expressed, along with a ribosome binding site and a polyadenylation site for transcriptional termination.

The transcriptional and translational control sequences in expression vectors to be used in transforming vertebrate cells are often provided by mammalian and vital sources. For example, commonly used promoters can be derived from polyoma, adenovirus 2, and simian virus 40 (SV 40). Further, the human genomic D4 receptor promoter, control and/or signal sequences may also be used provided such control sequences are compatible with the host cell chosen. In the current invention, both inducible and constitutive expression were tested.

An origin of replication may be provided either by construction of the vector to include an exogenous origin, such as may be derived from SV40 or other vital source (e.g., polyoma, adenovirus, VSV, or MPV), or may be provided by the host cell chromosomal replication mechanism. If the vector is integrated into the host cell chromosome, the latter may be sufficient.

D4 dopamine receptors made from synthetic genes in accordance with the present invention may be used for screening compounds for D4 dopamine receptor activity, or for determining the amount of a dopaminergic drug in a solution (e.g., blood plasma or serum). For example, host cells may be transformed with a vector of the present invention, D4 dopamine receptors expressed in that host, the cells lysed, and the membranes from those cells used to screen compounds for D4-dopamine receptor activity. Competitive binding assays in which such procedures may be carried out are well known. Intact cells may also be used to measure D4 receptor activation. By selection of host cells which do not ordinarily express a dopamine receptor, preparations of membranes containing D4 receptors made from synthetic genes can be obtained. Membranes obtained from such cells can be used in binding studies wherein the drug dissociation activity is monitored. Further, D4 dopamine receptor agonist and antagonists can be identified by procedures well known in the art.

Cloned genes and vectors of the present invention are useful to transform cells which do not ordinarily express the D4-dopamine receptor to thereafter express this receptor. Such cells are useful as intermediates for making cell membrane preparations useful for receptor binding assays, which are in turn useful for drug screening.

Initial attempts by the present inventors to use the polymerase chain reaction (PCR) to amplify regions of the D4 gene [SEQ ID NO: 2] from human genomic DNA and from first-strand cDNA prepared from SK-N-MC cells were unsuccessful probably because the D4 receptor gene has an inordinately high G+C content (73%). The high G+C content may make this gene prone to formation of very stable secondary structures or difficult to completely denature, either of which may result in inefficient PCR amplification. Attempts to overcome these obstacles using variations of the PCR, such as co-solvents (10% DMSO or 10% glycerol), base analogues (7-deaza-dGTP), and high-temperature annealing were also unsuccessful, even to obtain short lengths of DNA product (about 200 bp). To solve this problem, the present inventors designed and synthesized by chemo-enzymatic methods a modified gene coding for a dopamine D4 receptor [SEQ ID NO: 1]. The gene was synthesized using the techniques of gene splicing by overlap extension described in Horton et al. (1989) Gene 77:61–68 (the disclosure of which is herein incorporated by reference) with PCR amplification of long nucleotides. The synthetic D4 receptor gene [SEQ ID NO: 1] has a lowered G–C content and no introns, can be used to stably express synthetic D4 dopamine receptors in cultures of transformed eukaryotic cells, and retains the drag dissociation properties characteristic of human dopamine receptor D4. [SEQ ID NO: 3] The stable expression of these synthetic receptors provides for a ready supply of transformed eukaryotic cells producing the synthetic dopamine receptor for the characterization of antipsychotic drugs.

The Examples which follow are illustrative of specific embodiments of the invention, and various uses thereof. They are set forth for explanatory purposes only, and are not to be taken as limiting the invention.

Example 1

Gene Design

To modify the gene for the D4 receptor [SEQ ID NO: 2], the SILENT program (GCG DNA Sequence Analysis Software, Madison, Wis.) was used to find potential unique restriction sites in the original gene. The sequence of the original gene was then changed to incorporate additional unique sites approximately every 50 base pairs (bp). The amino acid sequence of the receptor [SEQ ID NO: 3] was unaltered. The G+C content of the gene was then decreased by exchanging nearly every G or C for an A or T while maintaining the original amino acid sequence [SEQ ID NO: 3] and the unique restriction sites. The sequence was then searched for consensus splice donor (CAGGRRRT) and acceptor ((Y)$_{13}$AGG) sites and polyadenylation (AWTAAAA) signals and none were found. A consensus translation initiation signal (CCACC) was added to the 5' end immediately upstream of the initiation codon ATG.

The modified nucleotide sequence (SynD4) [SEQ ID NO: 1] is compared with the original human D4 sequence (HumD4) [SEQ ID NO: 2] in FIGS. 1A and B. The line labeled Diff. shows the bases that were changed to lower the G+C content of the gene. The final G+C content of the gene was 50%, compared to 73% for the coding region of the original sequence. Decreasing the G+C content allowed the use of the polymerase chain reaction (PCR) in the synthesis of the D4 gene. The nucleotide [SEQ ID NO: 1] and amino acid [SEQ ID NO: 3] sequence of the modified gene is shown in FIGS. 2A, B, C, D, E, F with the positions of the unique restriction sites. The amino acid sequence is identical to that of the published D4 receptor (shown at the third line of FIGS. 1A to 1E). The unique sites can be used for mutagenesis and structure-function analysis of the receptor. The HindIII sites at the 5' and 3' ends of the complete gene used for subcloning are not shown.

Example 2

Oligonucleotide Synthesis

For synthesis, the synthetic D4 gene (1169 bp) [SEQ ID NO: 1] was divided into 3 sections of ~400 bp each. Two long oligonucleotide templates (oligos) greater than 200 bp each were synthesized on a 0.2 μmole scale on a 380B DNA Synthesizer (Applied Biosystems, Inc.) using β-cyanoethyl phosphoramidites. Release of the trityl protecting group during synthesis was monitored every 25 cycles to determine coupling efficiencies. The oligos were deprotected in concentrated $NH_4OH$ for 24 hours at 65° C. and purified by n-butanol extraction and ethanol precipitation as described in Sawadago, M., and Van Dyke, M. W. (1991) *Nucleic Acids Res.* 19: 674. The oligos were synthesized to include the 5' sense and 3' antisense sequence of half of each section. These templates were complementary at their 3' ends (~20 bp overlap) so that when annealed and extended with Taq polymerase, a double stranded DNA of ~400 bp was created. Two primers complementary to the 3' ends of the newly synthesized strands were then used to amplify the full length double stranded (~400 bp) DNA. The sequences of the templates and primers used to synthesize each of the sections are shown in FIGS. 3A, B, C, D, E, F.

Example 3

Polymerase Chain Reactions

GeneAmp PCR kits from Perkin Elmer Cetus were used. Temperature cycling was done in a Perkin Elmer Cetus DNA Thermal Cycler. For each section of the gene to be amplified, a 100 μl standard reaction was prepared with 1 μg of each oligo (2 templates and 2 primers). The template sequences were amplified by annealing at 60° C. for 1 minute, extending at 72° C. for 1 minute, and denaturing at 94° C. for 1 minute (3 cycles) followed by 22 cycles as above except annealing was done at 65° C. Final PCR products were digested with HindIII, gel purified (Gene Clean), and subcloned into Bluescript SK(+) for sequencing. Standard DNA manipulations were performed as described in Sambrook, J., Fritsch, E. F., and Maniatis, T. (1989) *Molecular Cloning*.

Example 4

Nucleotide Sequencing and Analysis of PCR Generated Products

Double stranded plasmid DNA was sequenced by the enzymatic method using T7 polymerase from U.S. Biochemicals (Sequenase). Oligonucleotide primers were located in Bluescript (flanking the insert) or were the same as used in the PCR amplification reactions. Sequence reactions were electrophoresed on one meter thermosrated gels prepared with acrylamide or Hydrolink. From 12 clones with inserts of the 5' section, four had the correct sequence. All seven clones of the middle section of the gene selected for sequencing had errors, but one clone contained only a single C to T transversion that is silent (no amino acid change). From eight clones of the 3' section of the gene, one was correct.

Example 5

Assembly of Synthetic D4 Gene

Insert DNA was isolated from clones containing correct sequence for each of the three sections of the gene (the 5' insert was cleaved with HindIII and ClaI, the middle insert was cleaved with ClaI and PflMI, and the 3' insert was cleaved with PflMI and HindIII). The DNA inserts (1 μg of each insert) were gel purified and ligated together in a 10 μl reaction (16 hrs at 16° C.). Ligation was stopped by heating the reaction at 75° C. for 10 minutes. After cooling on ice, the ligated products were digested with 20 units of HindIII at 37° C. for 1 hour to give a full length gene of 1169 bp [SEQ ID NO: 1]. After agarose gel electrophoresis, the DNA was isolated and subcloned into Bluescript SK(+).

Example 6

D4 Receptor Expression Constructs

The synthetic D4 gene [SEQ ID NO: 1] was isolated from Bluescript SK(+) by cleavage with HindIII and purified by agarose gel electrophoresis. Initial attempts to stably express the synthetic D4 gene [SEQ ID NO: 1] in CHO pro$^-$5 cells were unsuccessful, although these cells express D2 and D3 receptors quite well. We hypothesized that if synthetic D4 receptor expression were affecting cell growth or viability, an inducible expression system may allow for the isolation of stably transfected cell lines. The CHO LacI line and vector system was used for this purpose. The synthetic D4 gene [SEQ ID NO: 1] was subcloned into pGG668, an expression vector that contains a lac repressor binding site immediately downstream from the TATA box of the CMV promoter, both of which are 5' to unique HindIII and BamHI cloning sites. Orientation of the clone was determined by BamHI digestion. This vector also encodes a gene conferring resistance to hygromycin B. When this vector is used in CHO-K1 cells that have been engineered to constitutively express a bacterial lac repressor (LacI cells), gene expression can be induced by adding 100 μM isopropyl thiogalactoside (IPTG) to the growth medium. The synthetic D4 gene [SEQ ID NO: 1] was also subcloned into the HindIII site of the EBV-based vector pCEP4 (Invitrogen) for expression in HEK293 cells. This vector has a CMV promoter 5' to the cloning site, and encodes a gene conferring resistance to hygromycin B. This vector has been shown to replicate episomally at high copy numbers in this cell line (Yates, J. L., Warren, N., and Sugden, B. (1985) *Nature* 313:812–815). Orientation of the clone was determined by BamHI digestion.

Example 7

Isolation of Stable Transfectants

CHO LacI cells were gown in αMEM, 2 mM L-glutamine, 100 U/ml penicillin G, 100 μg/ml streptomycin, 10% fetal bovine serum, and 500 μg/ml G418 (to maintain expression of the lac repressor). HEK293 cells were gown in DMEM high glucose, 4 mM L-glutamine, 100 U/ml penicillin G, 100 μg/ml streptomycin, and 10% fetal bovine serum. Both lines were gown in an atmosphere of 5% $CO_2$ at 37° C. CHO LacI cells and HEK293 cells were transfected with the appropriate expression construct with the liposome reagent DOTAP (BM), following the supplier's protocol. LacI cells were selected with 500 μg/ml G418 and 500 u/ml hygromycin B (Calbiochem). HEK293 cells were selected with 100 u/ml hygromycin B. After several weeks of selection, resistant colonies were isolated and gown for binding analysis.

Example 8

Preparation of Membranes

LacI synthetic D4 transfected cells were grown in the presence of 100 μM IPTG for 48 hours prior to harvest. Cells gown in 100 mm dishes were rinsed once with 5 mls of ice cold $Ca^{2+}/Mg^{2+}$ free PBS and scraped into 5 mls of the same buffer. Cells were pelleted (500 x g, 5 minutes), and resuspended in 25 mM Tris, 5 mM EDTA, 5 mM EGTA, pH 7.5 (TEE), and frozen in liquid nitrogen. After thawing, the cells were homogenized and centrifuged at 1,000 x to remove nuclei and unbroken cells. The supernatant was centrifuged at 20,000 x g, the membrane pellet was washed once with TEE, resuspended in binding buffer, and frozen in liquid nitrogen. Membrane aliquots were stored at −70° C.

Example 9

Radioligand Binding Assay

Binding assays were carried out in a final volume of 1 ml of 20 mM HEPES, pH 7.5, 150 mM NaCl, 10 mM $MgCl_2$, 1 mM EDTA, including ($^3$H)spiperone (Amersham, 119 Ci/mmol) and vehicle or 20 µM (+)butaclamol, to determine nonspecific binding. Incubations were for 1 hour at 30° C. Assays were stopped by filtration through Whatman GF/B filters followed by 2×10 ml washes with ice cold 50 mM Tris, pH 7.5. The filters were counted by liquid scintillation spectroscopy.

Twenty-four hygromycin resistant LacI cell lines which had been induced to express synthetic D4 receptors with IPTG were assayed by single-point binding analysis, with expression ranging from ~20 to 236 fmol/mg protein of ($^3$H)-spiperone binding sites. The highest expressing line, D4–19, was selected for saturation binding analysis. Scatchard transformation of the data gave a $K_d$ of 158 pM and a $B_{max}$ of 260 fmol/mg protein. To determine if sustained synthetic D4 receptor expression was detrimental to cell growth or viability we continuously induced synthetic D4 receptor expression in the D4–19 line for 27 days with fresh media containing 100 µM IPTG added every 2–4 days. Continuous induction had no effect on receptor density, which was maintained at values between 227 fmol/mg protein to 330 fmol/mg protein over the course, assayed every 2–4 days. This indicated that expression of the synthetic D4 receptor was not limited to inducible expression systems.

Thirty-eight hygromycin resistant HEK293 lines were assayed in the same manner as the LacI lines and expression ranged from ~20 to 720 fmol/mg protein ($^3$H)-spiperone binding sites. The highest expressing line, D4–24, was selected for saturation binding analysis with [$^3$H]spiperone. Scatchard analysis of the data gave a $K_d$ of 100 pM and a $B_{max}$ of 736 fmol/mg protein (FIG. 4). Synthetic D4 receptor expression in the D4–24 cell line remains constant for up to at least 12 passages of the cells, over a period of 10 weeks (FIG. 5).

Example 10

Functional Assay for D4 Inhibitors - cAMP Assays

The synthetic D4 gene [SEQ ID NO: 1] can also be used in other assays to screen compounds as inhibitors of D4 receptor activation. In these assays, a compound is added to a transformed eukaryotic cell and an assay is performed to detect a D4 receptor mediated signaling event such cAMP inhibition, a change in the extracellular acidification rate, or a change in the lipid metabolism of the cell, for example, arachidonic acid secretion. If there is no effect on the D4 receptor mediated signaling event, then a test is performed to test the compound for its ability to inhibit the D4 receptor signaling event. One such assay is the inhibition of cAMP accumulation by dopamine in D4–19 Chinese Hamster Ovary cells expressing D4 receptors. In this assay, clozapine is used as the antagonist.

AMP accumulation was measured in intact D4–19 cells plated at a density of 15,000 cells/well in a 24 well plate 48 hours prior to the experiment. The cells were incubated in serum free medium 1 hour prior to the experiment. Fresh medium (0.5 ml) containing 100 µM forskolin, 100 µM IBMX and varying concentrations of drugs were added to each well and cAMP was allowed to accumulate for 15 minutes at 30° C. The reactions were terminated by the removal of the medium and the addition of 100 µl cold 7.5% (TCA) trichloroacetic acid. The samples were diluted by the addition of 1.0 ml 50 mM sodium acetate, pH 6.2 and aliquots were assayed by RIA using Biomedical Technologies Incorporated cAMP RIA kit.

cAMP accumulation was measured in forskolin stimulated cells as described in methods. Dopamine (10 µM) was added to 3 wells (DA). Dopamine (10 µM) and clozapine (10 µM) were both added to 3 wells (DA+CLOZ) and clozapine alone (10 µM) was added to 3 wells (CLOZ). The bars are the averages of the three wells expressed as the percentage of the forskolin response.

In summary, we have synthesized a modified gene that codes for the human D4 dopamine receptor [SEQ ID NO: 3]. The synthetic gene [SEQ ID NO: 1] has been stably expressed in CHO cells using an inducible expression system, and in HEK293 cells constitutively. The stable expression of this modified gene will facilitate pharmacological and functional studies of the D4 receptor.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | |
|---|---|---|---|---|---|
| GGTAACAGAT | CTACTGCAGA | CGCAGACGGA | CTACTTGCTG | GAAGAGGTCC | AGCTGCAGGA 60 |
| GCTTCTGCTG | GAGCATCCGC | TGGACTTGCT | GGTCAAGGAG | CTGCAGCTTT | AGTTGGTGGA 120 |
| GTGTTGTTAA | TTGGTGCAGT | ATTAGCTGGA | AACAGTCTAG | TTTGTGTTAG | TGTAGCAACT 180 |
| GAAAGAGCTC | TACAAACACC | TACTAACTCA | TTCATAGTAA | GTTAGCAGC | TGCAGATTTA 240 |
| TTGCTAGCTT | TACTTGTACT | ACCATTATTT | GTTACTCAG | AAGTCCAGGG | TGGAGCTTGG 300 |
| CTCTTAAGTC | CAAGATTGTG | TGACGCACTC | ATGGCAATGG | ACGTCATGTT | GTGTACTGCT 360 |
| TCAATTTTCA | ACTTGTGTGC | AATCAGTGTA | GATCGATTCG | TAGCAGTTGC | TGTACCATTA 420 |
| AGATACAACA | GACAAGGAGG | CAGTCGACGC | CAGCTGCTTC | TCATTGGAGC | TACATGGTTA 480 |
| CTATCAGCGG | CCGTAGCTGC | ACCTGTACTG | TGTGGATTGA | ATGATGTTAG | AGGAAGGGAT 540 |
| CCAGCTGTAT | GTAGATTGGA | AGATAGAGAT | TATGTAGTTT | ACTCGAGTGT | ATGTAGTTTC 600 |
| TTTCTACCAT | GTCCATTAAT | GTTGCTACTT | TACTGGGCAA | CATTCAGAGG | ACTGCAGAGA 660 |
| TGGGAAGTTG | CACGTCGTGC | AAAGTTACAT | GGAAGAGCAC | CAAGAAGACC | TAGTGGACCT 720 |
| GGACCACCTA | GTCCAACACC | TCCAGCTCCA | AGATTACCTC | AAGATCCTTG | TGGGCCCGAC 780 |
| TGTGCTCCTC | CAGCACCTGG | TTTACCTCCA | GATCCTTGTG | GTTCTAACTG | TGCTCCTCCA 840 |
| GATGCGGTCC | GAGCTGCAGC | TCTACCACCT | CAGACTCCAC | CTCAGACGCG | TAGGAGAAGG 900 |
| AGAGCTAAGA | TCACAGGAAG | GGAGAGGAAA | GCTATGAGGG | TCCTACCTGT | GGTCGTTGGT 960 |
| GCATTCTTGT | TATGCTGGAC | ACCATTCTTT | GTTGTGCACA | TCACACAAGC | ACTGTGTCCT 1020 |
| GCTTGCTCAG | TGCCACCTAG | ACTTGTCAGT | GCGGTCACCT | GGTTGGGTTA | CGTAAACTCA 1080 |
| GCACTCAATC | CTGTCATCTA | CACTGTATTC | AATGCTGAAT | TCAGAAATGT | CTTCAGAAAG 1140 |
| GCTCTAAGAG | CTTGCTGCTG | A | | | 1161 |

( 2 ) INFORMATION FOR SEQ ID NO:2:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| GGGAACCGCA | GCACCGCGGA | CGCGGACGGG | CTGCTGGCTG | GCGCGGGCC | GGCCGCGGG 60 |
| GCATCTGCGG | GGGCATCTGC | GGGGCTGGCT | GGGCAGGGCG | CGGCGGCGCT | GGTGGGGGGC 120 |
| GTGCTGCTCA | TCGGCGCGGT | GCTCGCGGGG | AACTCGCTCG | TGTGCGTGAG | CGTGGCCACC 180 |
| GAGCGCGCCC | TGCAGACGCC | CACCAACTCC | TTCATCGTGA | GCCTGGCGGC | CGCCGACCTC 240 |
| CTCCTCGCTC | TCCTGGTGCT | GCCGCTCTTC | GTCTACTCCG | AGGTCCAGGG | TGGCGCGTGG 300 |
| CTGCTGAGCC | CCCGCCTGTG | CGACGCCCTC | ATGGCCATGG | ACGTCATGCT | GTGCACCGCC 360 |
| TCCATCTTCA | ACCTGTGCGC | CATCAGCGTG | GACAGGTTCG | TGGCCGTGGC | CGTGCCGCTG 420 |
| CGCTACAACC | GGCAGGGTGG | GAGCCGCCGG | CAGCTGCTGC | TCATCGGCGC | CACGTGGCTG 480 |
| CTGTCCGCGG | CGGTGGCGGC | GCCCGTACTG | TGCGGCCTCA | ACGACGTGCG | CGGCCGCGAC 540 |
| CCCGCCGTGT | GCCGCCTGGA | GGACCGCGAC | TACGTGGTCT | ACTCGTCCGT | GTGCTCCTTC 600 |
| TTCCTACCCT | GCCCGCTCAT | GCTGCTGCTC | TACTGGGCCA | CGTTCCGCGG | CCTGCAGCGC 660 |
| TGGGAGGTGG | CACGTCGCGC | CAAGCTGCAC | GGCCGCGCGC | CCCGCCGACC | CAGCGGCCCT 720 |
| GGCCCGCCTT | CCCCCACGCC | ACCCGCGCCC | CGCCTCCCCC | AGGACCCCTG | CGGCCCCGAC 780 |

```
TGTGCGCCCC CCGCGCCCGG CCTCCCCCCG GACCCCTGCG GCTCCAACTG TGCTCCCCCC    840

GACGCCGTCA GAGCCGCCGC GCTCCCACCC CAGACTCCAC CGCAGACCCG CAGGAGGCGG    900

CGTGCCAAGA TCACCGGCCG GGAGCGCAAG GCCATGAGGG TCCTGCCGGT GGTGGTCGGG    960

GCCTTCCTGC TGTGCTGGAC GCCCTTCTTC GTGGTGCACA TCACGCAGGC GCTGTGTCCT   1020

GCCTGCTCCG TGCCCCGCG GCTGGTCAGC GCCGTCACCT GGCTGGGCTA CGTCAACAGC   1080

GCCCTCAACC CCGTCATCTA CACTGTCTTC AACGCCGAGT TCCGCAACGT CTTCCGCAAG   1140

GCCCTGCGTG CCTGCTGCTG A                                              1161
```

(2) INFORMATION FOR SEQ ID NO:3:

(i) SEQUENCE CHARACTERISTICS:
  (A) LENGTH: 387 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:3:

```
Met Gly Asn Arg Ser Thr Ala Asp Ala Asp Gly Leu Leu Ala Arg
  1               5                  10                  15

Gly Pro Ala Ala Gly Ala Ser Ala Gly Ala Ser Ala Gly Leu Ala Gly
                 20                  25                  30

Gln Gly Ala Ala Ala Leu Val Gly Val Leu Leu Ile Gly Ala Val
                 35                  40                  45

Leu Ala Gly Asn Ser Leu Val Cys Val Ser Val Ala Thr Glu Arg Ala
 50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                 85                  90                  95

Gln Gly Gly Ala Trp Leu Leu Ser Pro Arg Leu Cys Asp Ala Leu Met
                100                 105                 110

Ala Met Asp Val Met Leu Cys Thr Ala Ser Ile Phe Asn Leu Cys Ala
                115                 120                 125

Ile Ser Val Asp Arg Phe Val Ala Val Ala Val Pro Leu Arg Tyr Asn
    130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
                180                 185                 190

Val Val Tyr Ser Ser Val Cys Ser Phe Phe Leu Pro Cys Pro Leu Met
                195                 200                 205

Leu Leu Leu Tyr Trp Ala Thr Phe Arg Gly Leu Gln Arg Trp Glu Val
                210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
                260                 265                 270

Pro Cys Gly Ser Asn Cys Ala Pro Pro Asp Ala Val Arg Ala Ala Ala
```

-continued

```
                  275                           280                           285
        Leu  Pro  Pro  Gln  Thr  Pro  Pro  Gln  Thr  Arg  Arg  Arg  Arg  Arg  Ala  Lys
             290                           295                           300

Ile  Thr  Gly  Arg  Glu  Arg  Lys  Ala  Met  Arg  Val  Leu  Pro  Val  Val  Val
        305                           310                           315                      320

Gly  Ala  Phe  Leu  Leu  Cys  Trp  Thr  Pro  Phe  Phe  Val  Val  His  Ile  Thr
                            325                           330                      335

Gln  Ala  Leu  Cys  Pro  Ala  Cys  Ser  Val  Pro  Pro  Arg  Leu  Val  Ser  Ala
                       340                           345                      350

Val  Thr  Trp  Leu  Gly  Tyr  Val  Asn  Ser  Ala  Leu  Asn  Pro  Val  Ile  Tyr
                  355                           360                      365

Thr  Val  Phe  Asn  Ala  Glu  Phe  Arg  Asn  Val  Phe  Arg  Lys  Ala  Leu  Arg
             370                           375                      380

Ala  Cys  Cys
        385
```

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
CACTATAAGC TTCCACCATG GGTAACAGAT CTA                                        33
```

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
AGTCACATCT AGCTAAGCAT CTTCGAATAT CAC                                        33
```

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
CACTATAAGC TTATCGATTC GTAGCAGTTG CTG                                        33
```

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CACGAGGAGG TCGTGGACCT TCGAATATCA C        31

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CACTATAAGC TTCCAGCACC TGGTTTACCT CC       32

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TTCCGAGATT CTCGAACGAC GACTTCGAAT ATCAC    35

What we claim is:

1. A DNA encoding a dopamine receptor, wherein said DNA is characterized as comprising the nucleotide sequence of SEQ ID NO:1.

2. A DNA according to claim 1 wherein the dopamine receptor encoded thereby is a D4 dopamine receptor.

3. A cloning vector comprising a DNA encoding a dopamine receptor, wherein said DNA is characterized as comprising the nucleotide sequence of SEQ ID NO:1.

4. A recombinant expression vector comprising the DNA of claim 1, wherein the vector expresses the synthetic dopamine receptor D4 in a transformed eukaryotic cell culture.

5. A eukaryotic cell culture transformed with the expression vector of claim 4, wherein the transformed eukaryotic cell culture expresses the synthetic dopamine receptor D4.

* * * * *